United States Patent [19] [11] 3,984,307
Kamentsky et al. [45] *Oct. 5, 1976

[54] COMBINED PARTICLE SORTER AND SEGREGATION INDICATOR

[75] Inventors: Louis A. Kamentsky, Briarcliff Manor; Isaac Klinger, Yorktown Heights, both of N.Y.

[73] Assignee: Bio/Physics Systems, Inc., Mahopac, N.Y.

[ * ] Notice: The portion of the term of this patent subsequent to Aug. 6, 1991, has been disclaimed.

[22] Filed: Aug. 5, 1974

[21] Appl. No.: 494,627

Related U.S. Application Data

[63] Continuation-in-part of Ser. No. 338,215, March 5, 1973, Pat. No. 3,827,555.

[52] U.S. Cl. .................... 209/74 R; 250/222 PC; 356/39; 324/71 CP
[51] Int. Cl.² ........................................ G01N 21/26
[58] Field of Search ............... 209/3, 4, 74, 111.6, 209/111.7, 111.8, 74, 110.5; 137/807; 210/65, 85; 235/92 V, 92 CP; 250/222 PC; 324/34, 61, 71 CP; 356/39; 198/38

[56] References Cited
UNITED STATES PATENTS

| 2,333,791 | 11/1943 | Hutchison | 235/92 PC |
| 2,656,508 | 10/1953 | Coulter | 324/71 CP |
| 3,269,419 | 8/1966 | Dexter | 137/81.5 |
| 3,362,421 | 1/1968 | Schaffer | 137/81.5 |
| 3,426,879 | 2/1969 | Walker | 194/DIG. 26 |
| 3,508,654 | 4/1970 | Glaettli | 210/85 |
| 3,508,655 | 4/1970 | Kamentsky | 210/85 |
| 3,560,754 | 2/1971 | Kamentsky | 209/111.5 X |
| 3,710,933 | 1/1973 | Fulwyler | 209/111.7 X |
| 3,743,090 | 7/1973 | Brown et al. | 209/74 |
| 3,827,555 | 8/1974 | Kamentsky et al. | 209/111.7 |

Primary Examiner—Robert B. Reeves
Assistant Examiner—Joseph J. Rolla
Attorney, Agent, or Firm—Curtis Ailes

[57] ABSTRACT

Small particles to be sorted are entrained in a stream of fluid and particle differences are detected to control a sorter located downstream. The sorter is effective to switch the particle carrying fluid to one of two different paths determined by the particle differences to thereby accomplish the sort. A particle detector is positioned to detect the passage of particles through one of said paths in order to verify that the sorting operation has occurred.

11 Claims, 3 Drawing Figures

COMBINED PARTICLE SORTER AND SEGREGATION INDICATOR

CROSS-REFERENCES TO RELATED APPLICATIONS

This application is a continuation-in-part of co-pending patent application Ser. No. 338,215 filed Mar. 5, 1973 for a PARTICLE SORTER WITH SEGREGATION INDICATOR, now U.S. Pat. No. 3,827,555 issued Aug. 6, 1974, and assigned to the same assignee as the present application.

This application also discloses subject matter which is described and claimed in a related U.S. Pat. No. 3,791,517 issued Feb. 12, 1974, resulting from a patent application filed Mar. 5, 1973 for a DIGITAL FLUIDIC AMPLIFIER and assigned to the same assignee as the present application.

This application also discloses subject matter described and claimed in a related U.S. Pat. No. 3,705,771 dated Dec. 12, 1972 for a PHOTOANALYSIS APPARATUS.

This invention relates to apparatus for sorting small particles such as biological cells which may be microscopic in size. More particularly, the apparatus is capable of sorting such particles having different characteristics into different containers or receptacles with a high degree of accuracy.

In recent years, accurate high speed machines have been devised for measuring and indicating various characteristics of small particles such as biological cells. One such machine is described and claimed, for instance, in U.S. Pat. No. 3,705,771 dated Dec. 12, 1972 for a PHOTOANALYSIS APPARATUS, and assigned to the same assignee as the present application. However, there is a continuing important need for a machine which will very accurately and very rapidly sort such particles into two or more groups having different characteristics. This sorting function is particularly needed for purposes of medical diagnosis, and for medical research. There are many different particle characteristics which can be the basis for the sorting or segregation. The sorting is particularly valuable in instances where the particles or cells having the unique characteristics are present in a very small proportion to the total, making it difficult to obtain information about the unique particles without physically separating those particles from the main body of particles in which they occur.

The present invention is particularly useful in conjunction with apparatus disclosed in the above-mentioned U.S. Pat. No. 3,791,517. The present invention is disclosed in combination with the apparatus of the above-mentioned patent, but it is understood that the present invention is also useful in combination in other sorting apparatus.

One of the most serious problems in particle sorters for very small particles is the difficulty in determining whether or not the apparatus is operating correctly to provide the desired segregation of sorted particles. This problem is particularly serious with particle sorters capable of very rapid operation.

Accordingly, it is one object of the present invention to provide an improved particle sorter which incorporates means for verifying that the sorting operation has taken place.

In particle sorting apparatus, the mode of operation may include the entrainment of the particles to be sorted in a stream of fluid, detection of differences in particle characteristics as the stream passes a detection station, and then transmission of the resultant detection signals to a sorting means located downstream of the detection station. The precise timing of the signals to the sorting means from the detection station is vital to the accurate operation of the apparatus. The required timing is dependent upon the velocity of the particle carrying fluid stream.

Accordingly, it is another object of the present invention to provide a means for indicating the duration of the interval for the passage of a particle from the detection station to the sorting means in order to determine the exact timing for the operation of the sorting means.

Further objects and advantages of the invention will be apparent from the following description and the accompanying drawings.

In carrying out the invention there is provided an improved particle sorting apparatus for sorting very small particles comprising a housing defining a detection chamber with means for moving a fluid in which the particles are suspended through said housing in a stream. A detection means is associated with said detection chamber for detecting differences in particle characteristics and operable to provide electrical signals which vary in accordance with said differences in particle characteristics. A sorting means is positioned downstream from said detection chamber housing, said sorting means being connected to said detection means and being operable in response to said electrical signals from said detection means to segregate particles having predetermined differences in particle characteristics from the stream of particles. Said particle sorting means defines at least two alternate paths of egress of particles therefrom, one of said paths representing particles segregated thereby and the other of said paths representing particles not to be segregated from the stream. The apparatus includes the combination of a light source and a photoelectric detector associated with one of said paths to determine the passage of particles therethrough in order to verify the sorting operation of the apparatus.

Figure 1:
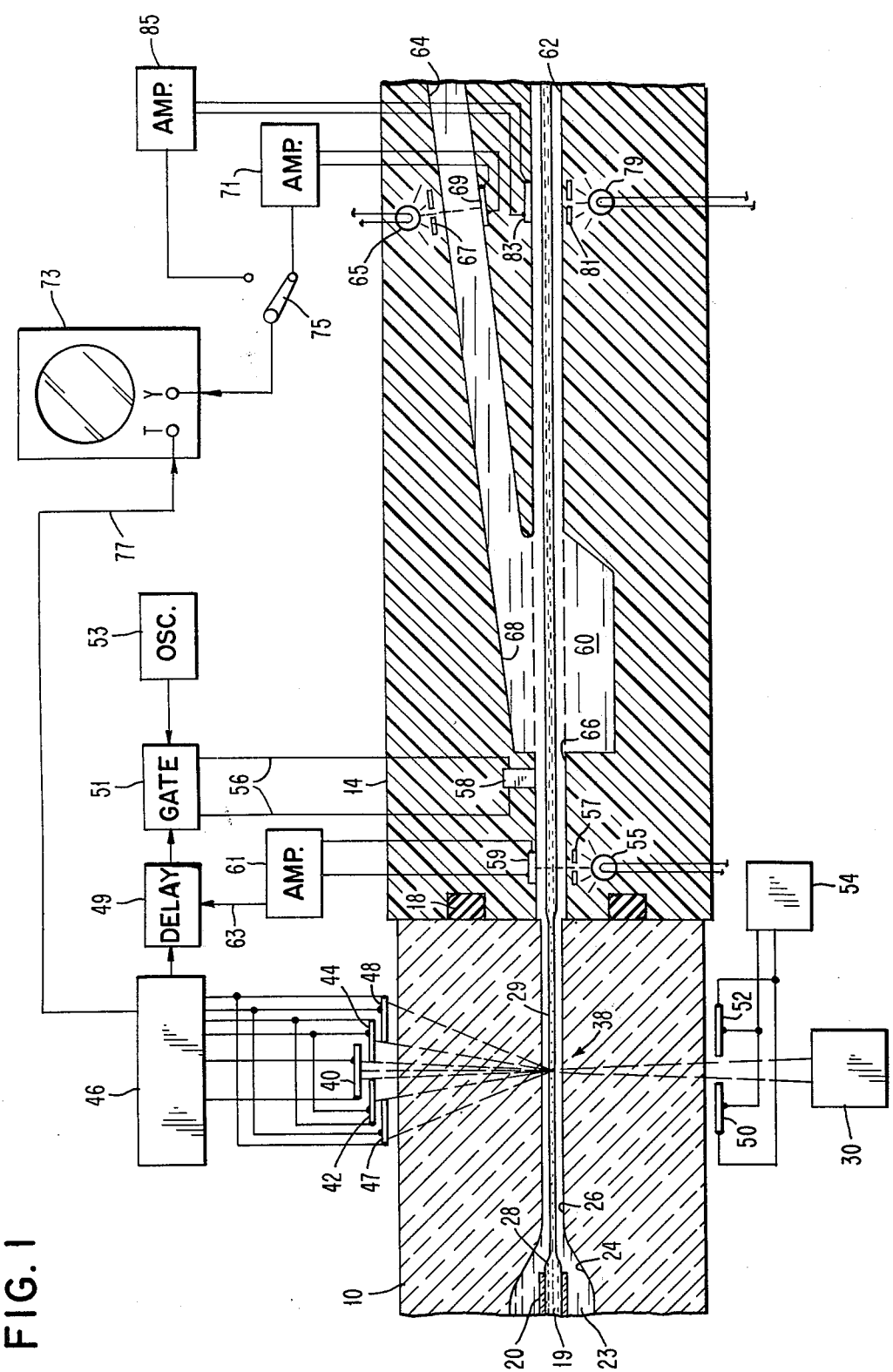
FIG. 1 is a schematic side view, partly in section, illustrating a preferred embodiment of the invention.

Referring more particularly to FIG. 1, there is shown an optical chamber formed by a glass tube member 10 which is clamped by means not shown to a digital fluidic switch chamber housing member 14, the two members being sealed together by a liquid-tight annular seal 18. The liquid 19 containing the particles to be observed enters the apparatus through a tube 20 centrally disposed within the funnel-shaped entrance portion 24 of the cylindrical central bore 26 of the member 10. Another liquid 23 also enters the mouth 24 of the central bore 26 and forms a sheath of liquid for the liquid 19 containing the particles.

The velocity and volume of flow of the particle-bearing liquid 19 and the sheath liquid 23 entering the mouth 24 of the central bore 26 are such as to cause the stream of particle-bearing liquid to be narrowed down, as shown at 28, into a very narrow stream 29 having a maximum dimension of the same order of magnitude as the maximum dimension of the particles being carried by the stream. For instance, this dimension may be in the order of 25 microns. The particles of greatest interest are often somewhat smaller than this, being in the range from 1 to 10 microns in diameter. The funnel-shaped entrance portion 24 of the cylindrical member 10 is preferably provided with an exponential function shape to provide for smooth non-turbulent flow of the liquids at the critical position 28 where the particle-carrying liquid is narrowed down. Typically, the particle-carrying liquid may be an aqueous solution and the sheath liquid 23 may be water.

The stream 29 of particles is illuminated by a beam of light emitted by a light source 30 which preferably consists of a laser together with an appropriate system of lenses as described more fully in the above-mentioned patent. One satisfactory type of laser, for instance, is a helium-neon laser. The laser and the associated lenses provide a very narrow beam in which the pattern of the illumination of the beam at point 38 where it strikes the particles is preferably a very narrow ellipse which appears to be a thin line of light transverse to the stream of particles.

Electrical photoresponsive pick-up elements are arranged around the outside of cylindrical chamber member 10 to detect different optical reactions of each particle to illumination from the beam. These elements are illustrated at 40, 42, 44, 47, and 48 which are all connected to provide signals to an apparatus 46, and elements 50 and 52 connected to provide signals to apparatus 54. The apparatus 54 may be combined with the apparatus of 46, but is separately shown to simplify the drawing. The apparatus 46 may include amplifiers, logic circuitry, digital counters, and electronic display devices. The circuits within the apparatus 46 may be carried out in accordance with the teachings of a prior U.S. Pat. No. 3,662,176 issued May 9, 1972 on an invention of Louis A. Kamentsky and Isaac Klinger for A PHOTO-OPTICAL PARTICLE ANALYSIS METHOD AND APPARATUS which is assigned to the same assignee as the present application. The apparatus 46 is sometimes referred to hereinafter as "circuits 46."

When a unique particle characteristic is detected which signifies the presence of a unique particle which is to be segregated from the other particles, the detection circuits 46 send out an electrical signal through a delay circuit 49, a gate circuit 51, and connections 56 to an electrical transducer 58 which is mounted within the fluidic switch housing 14. This causes a switching of the particle-carrying stream from one outlet port to another.

The fluidic amplifier housing 14 defines a switching chamber 60 having a first outlet port 62, and a second outlet port 64. The flow of liquid through the optical chamber 10 is in a laminar (non-turbulent) mode. In the absence of a signal at the transducer 58, the stream of fluid emanating from the bore 26 of the chamber 10 continues to flow in a laminar mode into the inlet 66 of the fluidic amplifier housing 14, and continues in the laminar mode through the switching chamber 60, and out through the first outlet port 62, which is in direct axial alignment with the inlet 66. However, when the transducer 58 is energized, it induces turbulence into the liquid stream. In the presence of turbulence, the stream tends to attach itself to the nearest side wall 68. This "wall attachment" effect causes the stream to follow the side wall 68 to the second outlet port 64.

The wall attachment effect is sometimes referred to as the "Coanda effect" in honor of the Rumanian engineer, Henry Coanda, who discovered it. This effect is well recognized in the literature as the basis for many fluidic digital switching devices. The wall attachment effect is caused by a "bubble" of low pressure adjacent to the exit of the nozzle formed by the inlet 66 at the beginning of the near side wall 68. This low pressure bubble causes the stream of liquid to bend towards the wall 68 and to become stable in this deflected course of travel. Thus, as long as the stream remains turbulent, by reason of the application of a signal to the transducer 58, the stream remains deflected to the second outlet port 64. However, upon the discontinuance of the signal to transducer 58, laminar flow is reestablished, the wall attachment effect disappears, and the stream returns to the first outlet port 62.

The speed of operation of the circuits 46 in providing a signal to the transducer 58 is properly correlated with the speed of the liquid stream of particles and the dimension between the optical detection point 38 and the transducer 58 to provide for switching of the desired particles from port 62 to port 64. The dynamic response in the speed of operation of the fluidic switch is also a factor. For this purpose, the delay circuit 49 is provided between the circuits 46 and transducer 58. The delay circuit 49 may be adjustable to properly correlate the timing of the signal to transducer 58 with the arrival of the particle to be switched by the transducer. One of the important advantages of this preferred embodiment of the invention is that the response of the system is extremely rapid since the transmission of signals is accomplished entirely electrically to the very point in the inlet 66 of the fluidic switch where turbulence must be induced. This is in contrast to other fluidic switches in which a signal is transmitted through a column of fluid to the control point.

The transducer 58 is preferably a piezoelectric crystal which is capable of physical deformation in response to an applied voltage. The excitation signal applied to the crystal 58 is preferably an alternating current at a frequency corresponding to the natural resonant frequency of the crystal 58 and its surrounding fluid so as to provide maximum mechanical output in response to the available electrical input energy. Thus, the individual signals applied to the transducer 58 are usually in the form of bursts of alternating current gated by gate 51 from an oscillator 53. The resultant alternating mechanical changes in the piezoelectric crystal 58 are very efficient in inducing turbulence in the liquid stream so as to assure immediate initiation of the wall attachment effect.

While the transducer is shown as embedded in a side wall of the inlet nozzle 66 of the fluidic amplifier on the same side as the wall 68, it will be understood that the transducer may be effective also in other locations communicating with the inlet 66, or in the switching chamber 60 in close proximity to inlet 66. The piezoelectric crystal is preferred as the transducer for this purpose. However, other types of transducers, such as electromagnetically energized acoustic vibration transducers may be employed.

The optical chamber member 10 is a glass tube having a cylindrical inner bore 26. However, the interior cavities of the digital fluidic amplifier defined by the housing 14 may be circular or non-circular in cross-section, or essentially two-dimensional in nature. Thus, the inlet 66 may include a transition from a circular shape to a rectangular shape, or the inlet 66 may simply be rectangular in shape throughout its length, having a minimum cross-sectional dimension which is at least as great as the diameter of the bore 26 of the optical chamber 10. The transition of the stream of liquid from the circular cross-section bore 26 to the rectangular inlet 66 of the fluidic amplifier does not disturb the flow sufficiently to create turbulence. Thus, the stream retains its laminar-characteristic until it is made turbulent by the transducer 58. The interior cavities of the housing 14 can be rounded at the corners, and the inlet 66 and the outlet ports 62 and 64 can actually be circular in cross-section without interfering with the operation of the device as described above.

The ports 62 and 64 are connected to suitable collectors or containers, not shown. Either, or both, of the separate collected cell bearing liquids can be run through the apparatus again to accomplish an additional refinement in the sorting operation by again sorting for the same characteristic, or for still another characteristic. After a run is completed, the apparatus may be flushed with a saline solution or water. To assure complete collection of all of the unique cells sorted at port 64, flushing liquid may be applied at the inlet 23 while outlet port 62 is blocked so that all of the flushing liquid is necessarily directed through the outlet port 64, carrying any sorted particles which remained in the port 64 and the associated passage to the collector or container associated with that port. The apparatus is then preferably completely flushed to prevent contamination of a new sample with the remains of a completed sample.

A number of different characteristics of the particles may be optically detected in the chamber 10 and used as a basis for the sorting of the particles. For instance, the electrical photoresponsive pick-up element 40 is arranged in direct line with the beam to measure the degree of extinction of illumination by each particle. In the absence of a particle at the intersection of the beam, or in the absence of any substantial extinction, the beam strikes the element 40 without any substantial diminution.

As illustrated in the drawing, the beam diverges to a certain extent after having been converged at the center of the chamber at 38. The effective divergence in a practical embodiment has been limited to approximately 1° on each side of the center line of the beam as measured from the particle scanning point 38 at the center of the chamber. Thus, photoresponsive pick-up elements 42 and 44 are arranged on opposite sides of the direct beam and can be used to measure illumination scattered out of the direct beam by the particles over a selected range of angles from 1° up to a predetermined angular limit. For instance, this range of angles may be from 1° to 9°. As shown in the drawing, the photoresponsive pick-up elements 42 and 44 may be electrically connected in parallel so that electrical signals resulting from illumination scattered on either side of the beam and detected by elements 42 and 44 will be registered at the electrical apparatus 46. Additional pairs of photoresponsive pick-up elements for detecting scattered light at other ranges of angles may be provided as shown at 47 and 48. For instance, this additional pair of pick-up elements may detect scatter over the scatter angle range from nine degrees to twenty-two degrees.

Scattering of illumination from the particles in the reverse direction, called "back scattering" can also be detected by photoresponsive elements 50 and 52 arranged on the same side of the chamber as the light source 30 and connected in parallel to an electrical pick-up and recording apparatus 54. Apparatus 54 may be combined with the apparatus 46, but it is shown separately here to simplify the drawing.

The portion of the apparatus for detecting different particle characteristics as just described above may preferably be carried out in accordance with the teachings of the U.S. Pat. No. 3,705,771 mentioned above. In addition to detecting different particle characteristics by extinction and by scatter, distinctive particle characteristics may also be determined on the basis of fluorescent radiation reactions from the particles to illumination of the particles as taught in that prior patent. When fluorescent radiation reactions are desired, an argon ion laser may be used as the source of illumination. Furthermore, sophisticated combinations of particle measurement characteristics may be employed for controlling the particle sorting operation. For instance, electrical summations or differences of different signals may be employed at selected threshold values for determining when a particle should be segregated from the main stream. Such circuits are described in the aforementioned U.S. Pat. No. 3,662,176.

The features described above in connection with FIG. 1 are common to the above-mentioned U.S. Pat. No. 3,791,517. The remaining features described immediately below in connection with FIG. 1 are particularly important and unique with respect to the present invention.

A source of illumination such as a small incandescent lamp is provided, as indicated at 55, which directs a beam thrugh a central slit in an optical mask 57 and thus through the particle carrying stream to an optical pick-up element, or photocell, 59. The optical pick-up element 59 is connected to an amplifier 61 which may be connected at 63 to control the variable delay circuit 49. The illumination from the lamp 55 traversing the particle stream to the photoelectric pick-up element 59 is effective to detect the passage of particles in the particle stream. Since this combination including pick-up 59 is located near the transducer 58, it is in a position to measure the arrival of the particle upon which the transducer 58 is intended to be effective, and to thus measure the travel time of the particle from the initial detection point 38 to the transducer 58.

While the pick-up element 59 is not located at the identical position of the transducer 58, the travel time of particles from point 38 to pick-up element 59 is proportional to the travel time from point 38 to the transducer 58 so that the interval until the arrival of particles at pick-up element 59 is a measure of the travel time to the transducer 58. Thus, the signals from pick-up element 59 amplified by the amplifier 61 may be used to control the delay circuit 49 to provide an exact match of the operation of the electrical circuits energizing transducer 58 with the velocity of the particle-carrying liquid. This provides an important enhancement in the precision and accuracy of operation of the sorter.

In accordance with another feature, another light source in the form of an incandescent lamp 65 provides a beam of light through a slit in an optical mask 67 which crosses the passage for port 64 to a photoelectric pick-up element 69 which is connected to an amplifier 71. By means of this apparatus associated with the photoelectric pick-up 69, the passage of a particle through the port 64 can be detected so as to positively indicate that the sorting operation has been successfully accomplished with respect to that particle. A very useful means for indicating this success is a cathode ray oscilloscope 73 which is connected through a switch 75 to receive the amplified sort indication signal from the amplifier 71, preferably as a vertical deflection on the oscilloscope.

In order to provide a correlated horizontal sweep, the scope 73 is preferably connected through a connection 77 to receive from the circuits 46 an indication of the passage of the particle at the original detection point 38, the signal on 77 being used to trigger the initiation of the horizontal sweep on the scope 73. Thus, the vertical deflection caused by the signal from amplifier 71 will occur at a predictable horizontal position on the scope 73 which is related to the velocity of the particle-carrying liquid through the apparatus.

Alternatively, a similar detection of the passage of particles to the port 62 may be accomplished by the combination of a lamp 79, an apertured mask 81, a photoresponsive pick-up element 83, and an amplifier 85 connected thereto. The switch 75 is arranged to select the output from amplifier 71 or from amplifier 85 for indication on the oscilloscope 73.

The pick-up 83 for port 62 may be used to indicate that the particles passing through the port 62 have not been selected to be segregated into port 64. For instance, the apparatus may be checked for proper sorting operation by introducing a sample in which all particles are of a class which should be segregated into the port 64. With such a sample, whenever the sorting operation is begun, vertical deflections on the oscilloscope 73 derived from the pick-up element 83 for port 62 should disappear completely.

The signal from the pick-up element 83 may also be employed in place of the signal from pick-up element 59 for controlling the delay circuit 49. Assuming that the main body of particles in the initial liquid stream continues on through the discharge port 62, the time interval of travel of an individual particle from the initial detection point 38 to the vicinity of the pick-up element 83 will be a predictable function of the interval for the travel of an individual particle from point 38 to the transducer 58. Accordingly, the measurement available from pick-up element 83 is an appropriate signal for controlling the delay circuit 49 in order to properly time the gating of the signals to the transducer 58. The pick-up element 59 and the associated apparatus may be omitted from the system if the signal from pick-up element 83 is used to control the delay circuit 49.

It is not absolutely necessary, in order to obtain the advantages of these features to have a direct connection, such as connection 63, from one of the pick-up amplifiers to control the delay circuit 49. In other words, an open loop system may be employed in which the delay interval is measured, such as by the indication on the oscilloscope 73, and that measurement is then used to manually set the delay on the variable delay circuit 49. However, the direct connection 63 from the amplifier 61 to the delay circuit 49 provides the advantage of continuous and automatic adjustment of the delay to compensate for any fluctuation in the velocity of the particle-carrying stream.

In accomplishing the purposes of the pick-ups 69 and 83 in indicating the accomplishment of the sort function, it may also be useful to have counters attached for actuation from the amplifiers 71 and 85 for indicating and storing a registration of the numbers of the particles which have been sorted into the respective ports 62 and 64. It is contemplated that the circuits 46 may include counters for counting the total number of particles and also for counting particles having unique characteristics to be detected and upon which the sort is to be based. Accordingly, the counters attached to the amplifiers 71 and 85 which indicate the numbers of particles sorted into the two channels can be compared with the counts registered by the counters within the apparatus 46 to accurately determine the efficiency of the sorting operation.

It will be understood that the pick-up elements 59, 69, and 83, and the associated apparatus, are shown schematically in order to simplify and clarify the drawing. In a preferred embodiment of the invention, each of these combinations of apparatus is preferably rotated ninety degrees about the axis of the associated liquid channel so that the direction of the light beam in each instance is directly perpendicular to the plane of the section shown in the drawing. Thus, in such a preferred arrangement, the pick-up element 59, for instance, would appear on the wall of the inlet 66 directly behind the liquid stream. In such a preferred physical embodiment, the lamp 55 and the pick-up 59 can be arranged and positioned exactly at the axial position of the transducer 58 within the inlet 66 so as to provide an exact measurement of the interval until the arrival of a particular particle at the transducer 58.

The switching chamber 60, and the ports 62, 64, and 66 may preferably be formed by providing the chamber housing 14 in two parts, one part containing cavities to provide the chamber and ports, and the other part constituting a cover which is attached over the other part to enclose the cavities. Thus, the part of the housing 14 containing the cavities may contain the pick-up elements 59, 69, and 83 in the back walls thereof, and the light sources 55, 65, and 79, together with their associated optical masks, may be attached to, or be a part of, the cover member. These positions may, of course, be reversed.

Other modifications are also possible. For instance, fiber optics may be employed to carry the illumination from a lamp, such as 55, to the channel, such as 66, where it is needed. Instead, or in addition, fiber optics may be used to convey the light beam from the channel 66 to the photoelectric pick-up 59. The use of fiber optics may be particularly advantageous because of the space limitations in the vicinity of the channels being monitored, the optical fibers requiring much less space than the lamp and photoelectric pick-up elements. Also, light sources other than incandescent lamps may be employed.

Figure 2:
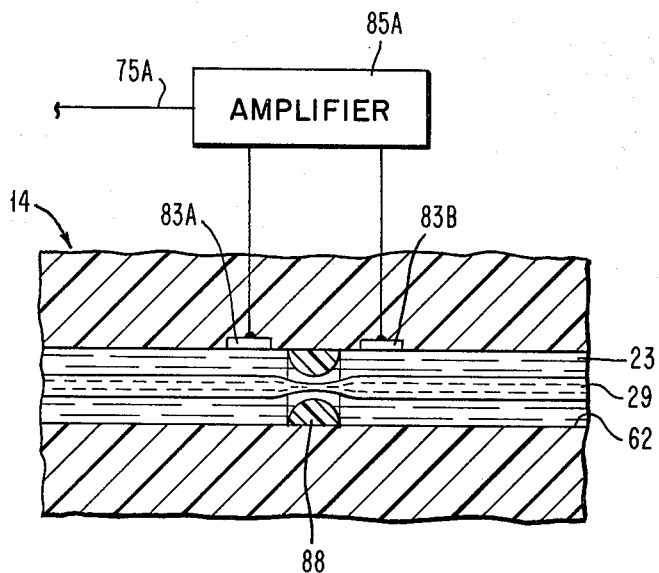
FIG. 2 is an enlarged detail view illustrating an alternative form of particle detector which is useful in the practice of the invention in detecting the passage of a particle through a path.
Figure 3:
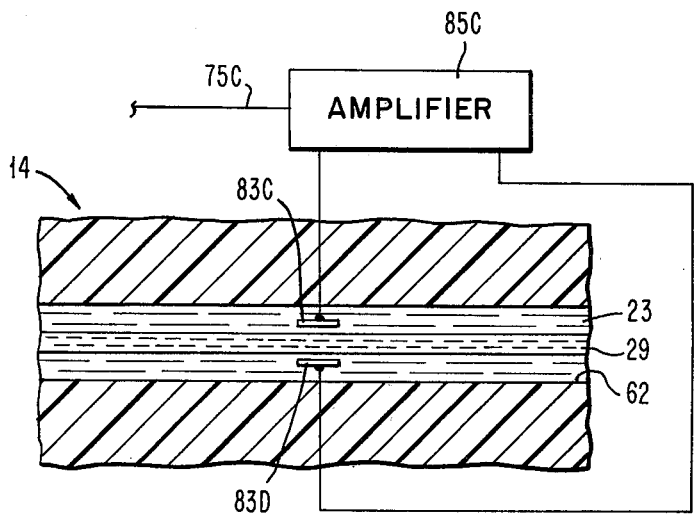
FIG. 3 is an enlarged detail view of still another alternative particle detector which is useful in the practice of the invention in detecting the passage of a particle through a path.

It is apparent that detectors other than the photoelectric detectors 59, 69, and 83 may be employed to fulfill the particle detection functions described above in connection with those detectors. For instance, the presence of individual particles may be detected by a change in electrical resistance in the particle stream, or by a change in the electrical capacitance of the particle stream due to the presence of a particle. FIG. 2 and FIG. 3 relate to such alternate detectors.

FIG. 2 illustrates an enlarged scale sectional detail view of an alternative electrical detector which can be used in place of any one of the photoelectric detectors 59, 69, and 83 as described above in connection with FIG. 1. It is specifically illustrated, by way of example, as installed in place of photoelectric detector 83 at port 62 of housing 14. It includes a modified amplifier 85A and detector elements 83A and 83B. A constriction is provided in the passage 62 by means of an orifice member 88 composed of electrical insulating material. The orifice 88 may be integrally molded within the housing 14, which is also composed of electrical insulating material. The detector operates by measuring the change in electrical resistance between electrode 83A and electrode 83B through the fluid within the passage 62. The amplifier 85A includes a current source together with means for measuring changes in the current due to changes in the resistance through the fluid between electrodes 83A and 83B caused by the passage of a particle through the stream having a conductivity different from the conductivity of the fluid in the stream. The constriction member 88 assures that the presence of a particle causes a substantial change in resistivity. The technical principles of this means of particle detection are well known. For instance, see U.S. Pat. No. 2,656,508 issued to W. H. Coulter on Oct. 20, 1953.

Upon detecting a resistance change due to the presence of a particle in the stream, the amplifier 85A provides an output signal at connection 75A which is intended to be connected to the switch 75 in FIG. 1, and through that switch to the cathode ray oscilloscope 73.

FIG. 3 illustrates another example of a particle detector different from the photoelectric detectors 59, 69, and 83 illustrated in FIG. 1. Again, FIG. 3 illustrates, by way of example, an enlarged sectional detail view of an alternative detector to replace the photoelectric detector 83. This structure includes electrodes 83C and 83D, which are schematically illustrated, are closely spaced on opposite sides of the central stream 29 within the channel 62, and are operable to detect changes in electrical capacity caused by the presence of a particle of dielectric constant different from the surrounding fluid. The amplifier 85C is operable to apply a voltage across the electrodes 83C and 83D, and to detect the capacity change between those electrodes due to the presence of a particle in stream 29 and to provide a signal on the output 75C which is to be connected to the switch 75 in FIG. 1, and thus to the oscilloscope 73.

Various alternative electrical detector structures may be employed for carrying out the detector principles described immediately above in connection with FIGS. 2 and 3. For instance, the structure of FIG. 3 may be alternatively employed with the resistivity change mode of operation explained in connection with FIG. 2.

In the related U.S. Pat. No. 3,791,517 listed above, various modifications of the particle sorter of FIG. 1 are disclosed and described. It will be understood that the particle detectors employing the photoelectric pick-up elements 59, 69 and 83 are equally applicable in combination in the modifications disclosed in that related patent. Similarly, the modified detectors of FIGS. 2 and 3 may also be used in combination with such modified particle sorting apparatus.

The optical detection chamber 10 of FIG. 1 is preferably composed of glass, and the switching chamber housing 14 may preferably be composed of a transparent synthetic resin material. While illustrated as separate housings which can be dissembled from one another, it is obvious that these housings can be combined in a unitary structure.

While this invention has been shown and described in connection with particular preferred embodiments, various alterations and modifications will occur to those skilled in the art. Accordingly, the following claims are intended to define the valid scope of this invention over the prior art, and to cover all changes and modifications falling within the true spirit and valid scope of this invention.

We claim:

1. An improved particle sorting apparatus for sorting very small particles comprising a housing defining a detection chamber, means for moving a fluid in which the particles are suspended through said housing in a stream, a particle characteristic detection means associated with said detection chamber for detecting differences in particle characteristics and operable to provide electrical signals which vary in accordance with said differences in particle characteristics, sorting means positioned downstream from said detection chamber, said sorting means being connected to said particle characteristic detection means and being operable in response to said electrical signals from said detection means to segregate particles having predetermined differences in particle characteristics from the stream of particles, said particle sorting means defining at least two alternate paths of egress of particles therefrom, one of said paths representing particles segregated thereby and the other of said paths representing particles not to be segregated from the stream, an indicating means coupled to receive signals from said particle characteristic detection means indicative of the presence of particles to be sorted, a path detector associated with one of said paths downstream from said sorting means to determine the passage of particles therethrough, said indicating means being coupled to said path detector to receive a signal therefrom in response to the passage of a particle through the path with which said path detector is associated, said indicating means being operable in response to said last-mentioned signal in correlation with the corresponding signal for that particle from said particle characteristic detection means to register the passage of that particle through said path in order to verify the sorting operation of the apparatus.

2. An apparatus as claimed in claim 1 wherein said path detector includes at least two electrodes spaced on opposite sides of the associated fluid path, and circuit means connected to said electrodes operable to measure changes in electrical capacitance between said electrodes caused by passage of particles therebetween.

3. A particle sorting apparatus as claimed in claim 1 wherein said path detector is associated with the path of particles segregated by said particle sorting means.

4. A particle sorting apparatus as claimed in claim 1 wherein said path detector is associated with the path representing particles not to be segregated from the stream.

5. An apparatus as claimed in claim 1 wherein
said indicating means comprises a cathode ray oscilloscope,
said particle characteristic detection means being coupled to said indicating means by a connection to said cathode ray oscilloscope to provide a signal to initiate the operation of an oscilloscope sweep circuit in response to the passage of a particle at said particle difference detection means,
and said oscilloscope being coupled to provide a visual indication of the signal from said path detector on an axis perpendicular to the axis of the sweep obtained from said sweep circuit.

6. Apparatus as claimed in claim 1 wherein
said sorting means comprises a digital fluidic amplifier having an inlet connected to the outlet of said detection chamber to receive the particle stream,
said fluidic amplifier including a switching chamber communicating with said inlet and at least two different outlet ports communicating with said switching chamber and defining said alternate paths of egress of particles therefrom,
said sorting means including an electrical transducer coupled to receive electrical signals from said detection means,
said fluidic amplifier being operable in response to signals received from said detection means through said electrical transducer to switch the fluid particle carrying stream entering the inlet thereof from a first outlet port representing one of said alternate paths to a second selected outlet port representing the other of said alternate paths.

7. An apparatus as claimed in claim 1 wherein
said path detector comprises at least two electrodes positioned and arranged for communication with the fluid within the associated path,
and circuit means connected to said electrodes for measuring changes in electrical resistance between said electrodes caused by a particle to thereby detect the passage of a particle through said path.

8. An apparatus as claimed in claim 7 wherein
the electrical path between said electrodes is physically constricted to enhance the resistance change signal caused by the passage of a particle therethrough.

9. An improved particle sorting apparatus for sorting very small particles comprising
a housing defining a detection chamber,
means for moving a fluid in which the particles are suspended through said housing in a stream,
a particle characteristic detection means associated with said detection chamber for detecting differences in particle characteristics and operable to provide electrical signals which vary in accordance with said differences in particle characteristics,
sorting means positioned downstream from said detection chamber,
said sorting means being connected to said particle characteristic detection means and being operable in response to said electrical signals from said detection means to segregate particles having predetermined differences in particle characteristics from the stream of particles,
said particle sorting means defining at least two alternate paths of egress of particles therefrom,
one of said paths representing particles segregated thereby and the other of said paths representing particles not to be segregated from the stream,
an indicating means coupled to receive signals from said particle characteristic detection means indicative of the presence of particles to be sorted,
a downstream detector associated with said stream of particle carrying fluid down stream from said detection means for providing an indication of the passage of a particle therethrough,
said indicating means being coupled to said downstream detector to receive a signal therefrom in response to the passage of a particle through the path with which said downstream detector is associated,
said indicating means being operable in response to said last-mentioned signal in correlation with the corresponding signal for that particle from said particle characteristic detection
to measure the interval between the signal from said particle characteristic detection means and the corresponding signal from said downstream detector to thereby measure the speed of a particle to be sorted as a basis for determining the timing of the operation of said sorting means.

10. Apparatus as claimed in claim 9 wherein there is provided
an adjustable delay means connected between said particle characteristic detection means and said sorting means for providing an adjustment in the timing between the actuation of said particle characteristic detection means and the resulting signal to said sorting means,
said delay being adjustable in accordance with the time interval determined by said downstream detector.

11. Apparatus as claimed in claim 9 wherein
said sorting means comprises a digital fluidic amplifier having an inlet connected to the outlet of said detection chamber to receive the particle stream,
said fluidic amplifier including a switching chamber communicating with said inlet and at least two different outlet ports communicating with said switching chamber and defining said alternate paths of egress of particles therefrom,
said sorting means including an electrical transducer coupled to receive electrical signals from said detection means,
said fluidic amplifier being operable in response to signals received from said detection means through said electrical transducer to switch the fluid particle carrying stream entering the inlet thereof from a first outlet port representing one of said alternate paths to a second selected outlet port representing the other of said alternate paths.

* * * * *

UNITED STATES PATENT AND TRADEMARK OFFICE
CERTIFICATE OF CORRECTION

PATENT NO. : 3,984,307
DATED : October 5, 1976
INVENTOR(S) : Louis A. Kamentsky and Isaac Klinger It is certified that error appears in the above-identified patent and that said Letters Patent are hereby corrected as shown below:

Column 6, line 41, "thrugh" should read --through--.

Column 12, line 25, after "detection", "means" should be inserted.

Signed and Sealed this

Fourth Day of January 1977

[SEAL]

Attest:

RUTH C. MASON
*Attesting Officer*

C. MARSHALL DANN
*Commissioner of Patents and Trademarks*